United States Patent
Mitchell et al.

(10) Patent No.: US 7,009,081 B2
(45) Date of Patent: Mar. 7, 2006

(54) N-METHYLATED AMINES FROM SELECTIVE VAPOR PHASE AMINATION OF AMINO ETHER ALCOHOLS

(75) Inventors: John William Mitchell, Allentown, PA (US); Richard Paul Underwood, Allentown, PA (US); Michael Edward Ford, Cooperburg, PA (US); Gamini Ananda Vedage, Bethlehem, PA (US); Hong-Xin Li, Lansdale, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 204 days.

(21) Appl. No.: 10/634,516

(22) Filed: Aug. 4, 2003

(65) Prior Publication Data

US 2005/0033091 A1    Feb. 10, 2005

(51) Int. Cl.
*C07C 209/16*    (2006.01)
(52) U.S. Cl. .................................................... 564/474
(58) Field of Classification Search ................ 564/474
See application file for complete search history.

(56) References Cited

U.S. PATENT DOCUMENTS

| | | | | |
|---|---|---|---|---|
| 4,153,581 A | * | 5/1979 | Habermann | 502/329 |
| 4,480,131 A | * | 10/1984 | Klier et al. | 564/480 |
| 4,642,381 A | * | 2/1987 | Klier et al. | 564/480 |
| 4,922,023 A | | 5/1990 | Fischer et al. | 564/479 |
| 5,756,558 A | | 5/1998 | Savoca et al. | 521/167 |
| 5,824,711 A | | 10/1998 | Kimock et al. | 521/129 |
| 5,874,483 A | | 2/1999 | Savoca et al. | 521/115 |
| 6,037,496 A | | 3/2000 | Carr et al. | 564/198 |
| 6,187,957 B1 | | 2/2001 | Meyer et al. | 564/473 |

FOREIGN PATENT DOCUMENTS

| | | |
|---|---|---|
| EP | 0 017 651 A1 | 10/1980 |
| EP | 0167872 | 3/1990 |
| EP | 0057884 | 4/1992 |
| EP | 0 765 892 A1 | 4/1997 |
| EP | 0 816 408 A1 | 1/1998 |
| EP | 0 877 016 A1 | 11/1998 |
| JP | 59134754 | 8/1984 |
| JP | 09020735 | 1/1997 |

OTHER PUBLICATIONS

Database CAPLUS on STN, Acc. No. 1995:848208, Shuikin et al., Izvestiya Akademii Nauk, Seriya Khimicheskaya (1993), Vo. 4, p. 799-800 (abstract).*

* cited by examiner

*Primary Examiner*—Brian Davis
(74) *Attorney, Agent, or Firm*—Mary E. Bongiorno

(57) ABSTRACT

A method for converting amino ether alcohols to amino ether amines by amination in the vapor phase with a catalyst comprising copper and zinc. The catalyst may also comprise an alkali, alkaline earth, or lanthanide element as a promoter.

17 Claims, No Drawings

N-METHYLATED AMINES FROM SELECTIVE VAPOR PHASE AMINATION OF AMINO ETHER ALCOHOLS

BACKGROUND OF THE INVENTION

The current invention relates to an improved process for the selective conversion of amino ether alcohols to amino ether amines. The amino ether amines are suitable as blowing catalysts and precursors for blowing catalysts for polyurethane foams.

Tertiary amine catalysts have been used in the production of polyurethanes. The tertiary amine catalysts accelerate both blowing (reaction of water with isocyanate to generate carbon dioxide) and gelling (reaction of polyol with isocyanate) and have been shown to be effective in balancing the blowing and gelling reactions to produce a desirable product.

Typical catalysts include amino ether amines, of which two examples are N,N,N'-trimethylbis(aminoethyl)ether (TMAEE) and bis(dimethylaminoethyl)ether (BDMAEE).

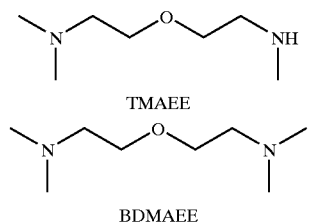

BDMAEE is an industry standard blowing catalyst for flex-molded polyurethane foams. Market and regulatory drivers have also created a need for emission-free, non-fugitive catalysts. Non-fugitive, reactive, functionalized analogs of BDMAEE can be produced from TMAEE, as described in U.S. Pat. No. 5,874,483 and U.S. Pat. No. 6,037,496. The reactive N—H group provides a point for further functionalization using standard synthetic techniques (e.g., aminopropylation, carbamoylethylation, ethoxylation, and propoxylation). The resulting functionalized amino ether amines, which contain a reactive site for chemically bonding into the growing polyurethane matrix during polymerization, are potential non-fugitive blowing catalysts, whose use may reduce odors and emissions during the manufacture and use of polyurethanes.

Amino ether amines have been prepared via catalytic amination of the corresponding amino ether alcohol with monomethylamine (MMA) or dimethylamine (DMA). For example, TMAEE and BDMAEE can be produced via amination of dimethylaminoethoxyethanol (DMAEE) with MMA or DMA, respectively:

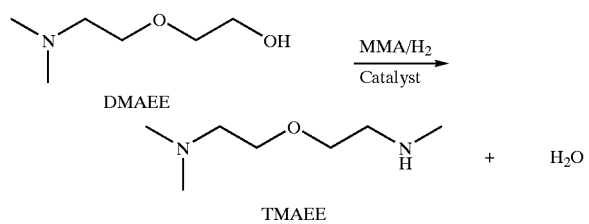

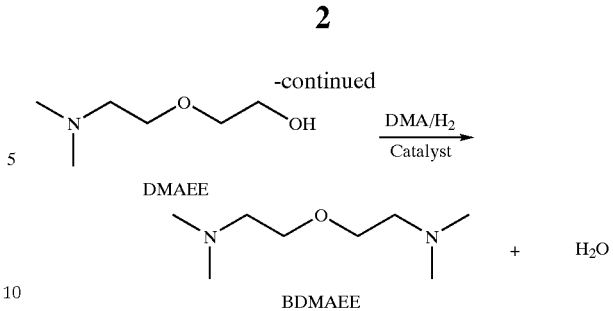

Current processes for substitution of alcohols with MMA or DMA typically rely on either acidic catalysts or liquid phase reductive amination with copper-containing catalysts.

U.S. Pat. Nos. 5,756,558; 5,824,711; 5,874,483; and 6,037,496 disclose material compositions for the production of polyurethane catalysts. These materials may be made from a TMAEE intermediate. U.S. Pat. No. 5,874,483 teaches, through example, that TMAEE can be produced via liquid phase amination of DMAEE with MMA in a batch reactor. JP 59,134,754 describes a process to produce BDMAEE via the batch amination reaction of DMAEE with DMA over copper catalysts (Cu/Cr or Raney Cu), followed by methylation using formaldehyde. The methylation step is utilized to remove byproduct TMAEE.

Further, liquid phase reductive amination with copper-containing catalysts is often impractical. The stability of copper catalysts is often poor, owing to the solubility of copper species in amine products, and this solubility also results in the contamination of the amine product with copper.

The production of DMAEE, a precursor to TMAEE, is recited in several U.S. patent references referring to aminating diethylene glycol (DEG) with DMA over copper catalysts to produce DMAEE, with BDMAEE co-produced at lower levels. U.S. Pat. No. 4,922,023 discloses a liquid phase process over Cu/Al catalysts. EP 167,872 (B1) discloses application of Cu/Al/carbonate catalysts. JP 09-20,735 describes a vapor phase process using a glycol-impregnated Cu catalyst. EP 057,884(B2) discloses a vapor phase process over Cu/Al catalyst, where a mixture of DEG, DMAEE, and DMA is fed to an atmospheric pressure reactor. U.S. Pat. No. 6,187,957 discloses use of a $Cu/TiO_2$ catalyst, containing metallic copper powder. This latter process, which can be run in either vapor or liquid phase, is shown to produce some TMAEE, but TMAEE is noted as an unwanted byproduct, with the major product again being DMAEE, with secondary co-produced BDMAEE.

U.S. Pat. No. 4,480,131 discloses a process for aminating certain short chain alkyl (or aryl) alcohols with primary amines over copper or palladium catalysts. This patent teaches that the methods recited therein minimize amine disproportionation and scrambling of alkyl groups during that amination process.

Notwithstanding this prior technology, there remains a need for improved processes for preparing amino ether amines by methods providing good selectivity, with the product having a low level of copper catalyst contamination.

BRIEF SUMMARY OF THE INVENTION

In one aspect, the invention is a method for converting an amino ether alcohol to an amino ether amine, the method comprising contacting a catalyst comprising at least one of zinc oxide and a zinc salt, and at least one of copper oxide and a copper salt, with a vapor phase mixture comprising the amino ether alcohol and an amine.

In another aspect, the invention is a method for converting dimethylaminoethoxyethanol to an amino ether amine. The method comprises contacting a catalyst with hydrogen gas to produce an active catalyst, and contacting the active catalyst with a vapor phase mixture comprising dimethylaminoethoxyethanol and at least one of methylamine and dimethylamine. The catalyst can comprise 20 to 70 wt % copper oxide, 20 to 65 wt % zinc oxide, and, optionally, 0.05 to 5 wt % of a promoter, such as potassium and/or cesium, based on total catalyst weight.

DETAILED DESCRIPTION OF THE INVENTION

The invention provides an improved process for the conversion of amino ether alcohols to amino ether amines. For example, the invention provides the production of N,N,N'-trimethylbis(aminoethyl)ether (TMAEE) and/or bis(2-dimethylaminoethyl)ether (BDMAEE) from the amination of dimethylaminoethoxyethanol (DMAEE). In one exemplary embodiment, the process involves the reaction of an amino ether alcohol with an amine in a continuous mode in a zone containing a Cu/Zn catalyst, at conditions such that the reactants are in the vapor phase. In another embodiment, addition of a promoter to the catalyst increases the selectivity of conversion of the amino ether alcohol to the desired amino ether amine.

The process of the present invention provides improvements in the selectivity, yield, and productivity of the desired product. One especially advantageous aspect of the invention is that the formation of intramolecular amination side products, such as the formation of N-methylmorpholine during the production of TMAEE, can be reduced to a very low level relative to the desired product. Also, since the vapor phase processing requires a lower reactor pressure and operates in a continuous mode, reactor construction and operation may be simplified. Copper leaching from the catalyst is essentially eliminated in vapor processing, resulting in longer catalyst life, minimal copper contaminants in the product, and alleviating need for equipment cleaning to remove deposited copper. Furthermore, addition of one or more promoters chosen from the Group 1 or 2 elements or early lanthanides, to the base Cu/Zn catalysts, can result in a substantial improvement in catalyst selectivity for the desired reaction vs. side reactions.

Reactor Configuration

Reactors suitable for use according to the invention may be any of a variety of types and sizes, with the provision that there be good contact between the vaporized feeds and catalyst While the reactions may be most simply carried out in a fixed bed, single tube, adiabatic reactor, other configurations that may be used include fixed bed reactors containing multiple tubes, with or without cooling, and fluidized bed systems. The amino ether alcohol may be fed to the reactor by any of various means know to the skilled artisan, including for example a metering pump. A second means of introduction is arranged for introducing the amine into the reactor, or the amine may be combined with the amino ether alcohol prior to introduction. Typically, hydrogen is co-fed to the reactor via a flow controller or other metering device to maintain the catalyst in an active state. These reactants, either separately or commingled, must be vaporized and/or heated to a sufficient temperature to ensure that they are in the vapor phase prior to contacting the catalyst. The products of the reaction are then condensed by cooling and may then be separated via distillation or other techniques known in the chemical engineering art.

Catalyst

Catalysts suitable for use according to this invention are any of a broad class of Cu/Zn materials. As used herein, the term "catalyst" will refer to a material that is charged to the reactor for the purpose of acting as a catalyst, but it will be understood that the actual catalytic species that are responsible for the conversion of amino ether alcohols to amino ether amines may represent a change in composition from the catalyst as charged. Typically, the catalyst will be treated with a reducing agent prior to performing the conversion of amino ether alcohol to amino ether amine. Such reduction may, according to the invention, be by any chemical means. Typically the reduction may be performed by contacting the catalyst with hydrogen at an elevated temperature. The hydrogen may be introduced as $H_2$ gas, or it may be formed by interaction of the catalyst with an organic compound, for example isopropyl alcohol. Typically the reducing agent is used to pre-treat the catalyst prior to use, and typically its introduction into the reactor is continued on either an intermittent or continuous basis during the amination reaction, to keep the catalyst in an active state.

Catalysts suitable for use according to the invention comprise a copper salt and/or oxide and a zinc salt and/or oxide. The weight ratio of Cu/Zn (as the metals) may be 0.3 to 6, preferably 0.4 to 3, more preferably 0.45 to 2.75. The copper and zinc salts or oxides may include as nonlimiting examples carbonates, hydroxides, and/or salts of carboxylic acids. In one exemplary embodiment, the catalyst comprises 20 to 70 wt % of CuO and 20 to 65 wt % of ZnO. In another exemplary embodiment, the catalyst comprises CuO, ZnO, $Al_2O_3$, and $SiO_2$. The content of $SiO_2$ in the catalyst may range from 0 to 40% by weight, preferably 0 to 10%. The content of $Al_2O_3$ in the catalyst may range from 0 to 40% by weight, preferably 0 to 20%. Other materials may be present in the catalyst as well. Catalysts comprising CuO, ZnO, and optionally $Al_2O_3$ and $SiO_2$, are commercially available, with exemplary products sold under the names G-132D, T-4581, and T-4322 by Süd-Chemie of Louisville, Ky., USA, and Cu0891, available from Engelhard Corp. of Iselin, N.J., USA. In one embodiment of the invention, the catalyst has a Cu/Zn ratio of about 0.8.

The catalyst may comprise a promoter to enhance the selectivity of the conversion of the amino ether alcohol to the desired amino ether amine. Promoters suitable for use according to the invention may be chosen from the alkali metals (Group 1 of the periodic table), alkaline earth metals (Group 2 of the periodic table), or early lanthanides (Group 3 of the periodic table, particularly those elements ranging from atomic number 57, lanthanum, to atomic number 65 terbium, with the exception of element number 61, promethium). Examples of suitable promoters include lithium, sodium, potassium, rubidium, cesium, magnesium, calcium, strontium, barium, lanthanum, cerium, praseodymium, neodymium, samarium, europium, gadolinium, and terbium. More preferred promoters include sodium, potassium, rubidium, cesium, magnesium, calcium, strontium, barium, lanthanum, cerium, praseodymium, neodymium, and samarium. Most preferred promoters are potassium, rubidium, cesium, magnesium, calcium, strontium, lanthanum, cerium, and praseodymium. Promoters may be present in the catalyst at a level of 0.05 to 5 wt %, preferably 0.2 to 2 wt %, most preferably, 0.3 to 1.5 wt %.

One exemplary method of adding promoters to catalysts is shown in Example 5. Although the example shows addition of nitrate salts of the promoter metal to an already-formed Cu/Zn catalyst, other sequences and modes of addition to form the final promoted catalyst may be used.

Amino Ether Alcohol

Amino ether alcohols suitable for conversion to amino ether amines according to the invention include compounds comprising an amine $NR^1R^2R^3$, wherein $R^1$ and $R^2$ each individually may be selected from the group consisting of H, a C1–C10 alkyl, a C6–C10 aryl, and a C6–C10 aralkyl. In one exemplary embodiment, both $R^1$ and $R^2$ are methyl. $R^3$ is a C4–C10 alkyl group having within it an ether linkage and also containing at least one hydroxyl group. The hydroxyl group or groups may be those of primary and/or secondary alcohols. In one exemplary embodiment, $R^3$ is a 2-alkoxyethyl group wherein the alkoxy group bears an OH substituent. In another embodiment, the alkoxy group of $R^3$ is 2-hydroxyethoxy.

Amine

Amines suitable for reaction with the amino ether alcohol according to the invention include $NHR^4R^5$, wherein $R^4$ and $R^5$ each individually is H, a C1–C10 alkyl, a C6–C10 aryl, or a C6–C10 aralkyl group, provided that no more than one of $R^4$ and $R^5$ is H. Exemplary amines include monomethylamine (MMA) and dimethylamine (DMA).

Process Conditions

The process of the current invention can be carried out at temperatures in the range of 120 to 300° C., and pressures in the range of 0 to 500 psig (101 to 3549 kPa). We have found that the process operates quite effectively in the range of 180 to 220° C. and 0 to 100 psig (101 to 791 kPa), although not restricted to these ranges. In one embodiment, the pressure ranges from 40 to 80 psig (377 to 653 kPa).

The amine and the amino ether alcohol can be co-fed to the reactor over a broad ratio range. The molar ratio of amine to amino ether alcohol can be from 0.3 to 8, preferably from 1 to 4. If hydrogen is fed to the reactor, it is typically fed at a molar ratio of 1 to 8, preferably 2 to 5, relative to amino ether alcohol. Rates of addition of amine and amino ether alcohol to the reactor vary according to a variety of factors, including the exact composition of these materials, the exact catalyst used, the temperature of the reactor, the pressure, and other variables. Determination of optimum conditions for any particular combination of these parameters is well within the ability of the skilled artisan.

The invention will be further clarified by a consideration of the following examples, which are intended to be purely exemplary of the use of the invention.

EXAMPLES

Comparative Example 1

Liquid Phase Amination of DMAEE with MMA to Produce TMAEE in a Batch Reactor, as Described in U.S. Pat. No. 5,874,483

A 2-liter stainless steel autoclave was batch charged with 499.4 g of DMAEE and 37.9 g of a $CuO/ZnO/Al_2O_3/SiO_2$ catalyst (G-132D from Süd-Chemie, with a typical composition of 53% CuO, 27% ZnO, 15% $Al_2O_3$, and 4% $SiO_2$). After purging the reactor with nitrogen and hydrogen ($H_2$), the catalyst was activated in situ under 812 psig of hydrogen at a temperature of 195° C. for 9 hr. The reactor was cooled to 25° C. and vented to ambient pressure. From a sample cylinder connected to a port in the reactor head, 177 g of MMA was batch charged using a 94-psig nitrogen head to assist in the transfer. After resealing the reactor and pressurizing it to 215 psig with hydrogen, the reactor was heated to 195° C., and kept at that temperature for 23.3 hr. The reactor was then cooled to 25° C., and 600.1 g of reaction product was recovered after filtration to remove the catalyst particles. The reaction product had a blue-green tint indicating that copper had leached from the catalyst into the liquid product. The reactor internals had noticeable copper deposition on metal surfaces, again indicating that copper leached from the catalyst. Gas chromatographic analysis, excluding water, methylamine, and lights (other components eluting before the N-methylmorpholine), showed that the reaction product contained 34.0% DMAEE, 3.1% N-methylmorpholine (NMM), 44.3% TMAEE, 1.6% BDMAEE, and 17% other products with elution times greater than BDMAEE. Thus, the observable DMAEE conversion, defined as 100-DMAEE, was 66.0%. The TMAEE selectivity, defined as TMAEE/conversion×100, was 67.1%. The TMAEE yield, defined as conversion/100×selectivity, was 44.3%. The reactor productivity, defined as TMAEE produced per unit time per mass of catalyst, was 0.25 g TMAEE/g cat-hr. This productivity in the batch liquid reactor does not include the time impact of catalyst reduction, feedstock charging, and catalyst filtration, which would all decrease the reported productivity.

Example 2

Vapor Phase Amination of DMAEE with MMA to Produce TMAEE in a Continuous Fixed Bed Reactor A fixed bed tubular reactor, equipped with a 10 cc quartz preheat bed, was charged with 9.2 g of the $CuO/ZnO/Al_2O_3/SiO_2$ catalyst described in Example 1. The reactor was pressurized with nitrogen to 300 psig, and then vented to ambient. The reactor pressure was maintained by means of a backpressure controller. The nitrogen purge was repeated two additional cycles, followed by three hydrogen purges. The reactor was then fed hydrogen at 500 scc/m and 300 psig. The reactor was heated at 1° C./minute with a resistance heater to 250° C., and held at that temperature for 4 hr to activate the catalyst. The temperature and pressure were set as shown Table 1. The hydrogen flow, metered via a mass flow controller, was adjusted to provide a 4/1 molar ratio of $H_2$/DMAEE. DMAEE was fed to the reactor under pressure, via a constant flow syringe pump. MMA was co-fed to the reactor under pressure, via a constant flow syringe pump, at an MMA/DMAEE molar ratio of 2/1. Effluent from the reactor was analyzed by gas chromatography (GC). After several GC samples, the composition of the mixture remains unchanged over time. Recovered product showed no sign of a blue-green tint, indicating that copper leaching had not occurred to any appreciable extent. The results obtained at two variations of this example are displayed in the following table, where performance characteristics are those defined in Example 1 above.

TABLE 1

| Ex. | DMAEE feed, ml/hr | T, °C. | P, psig | DMAEE Conversion, % | TMAEE Selectivity, % | TMAEE Yield, % | Productivity, g TMAEE/ g-cat-hr |
|---|---|---|---|---|---|---|---|
| 2A | 14.22 | 199 | 70.5 | 74.6 | 69.1 | 51.6 | 0.79 |
| 2B | 21.33 | 202 | 67 | 55.3 | 74.7 | 41.3 | 0.95 |

These experimental data show several advantages in fixed bed, continuous vapor phase operation, relative to the batch, liquid phase operation of Example 1. Operating in the same range of conversion, TMAEE selectivity, and yield were improved. Reactor productivity has increased by 3.2 to 3.8 fold. This implies that less operational time is required to produce a given volume of product, and waste generation can be reduced. Also, since the vapor phase processing allows use of a lower reactor pressure and operates in a continuous mode, construction and operation should be simplified. Finally, copper leaching from the catalyst was minimized in vapor processing, implying longer catalyst life, minimal copper contaminants in the product, and alleviating need for equipment cleaning to remove deposited copper.

Example 3

Vapor Phase Amination of DMAEE with DMA to Produce BDMAEE in a Continuous Fixed Bed Reactor A fixed bed tubular reactor, which contains a quartz preheat bed, was charged with 3.5 g of the CuO/ZnO/Al$_2$O$_3$/SiO$_2$ catalyst described in Example 1. The catalyst was activated in a manner similar to that in Example 2. The temperature was adjusted to 200° C., and the pressure set at 100 psig. The hydrogen flow was adjusted to provide a 2/1 molar ratio of H$_2$/DMAEE. DMAEE was fed to the reactor under pressure, via a constant flow syringe pump, at 0.89 ml/hr. DMA was co-fed to the reactor under pressure via a constant flow syringe pump, at a DMA/DMAEE molar ratio of 4/1. Effluent from the reactor was analyzed by GC. Analysis shows that the DMAEE conversion was 74.3%, BDMAEE selectivity was 64.1% and the BDMAEE yield was 47.6%. These results indicate that BDMAEE can be produced at good yield in a vapor phase amination of DMAEE with DMA in a continuous fixed bed reactor.

Example 4

Vapor Phase Amination of DMAEE with MMA to Produce TMAEE in a Continuous Fixed Bed Reactor with an Alternate CuO/ZnO Catalyst A fixed bed tubular reactor, equipped with a 10 cc quartz preheat bed, was charged with 8.8 g of a CuO/ZnO/Al$_2$O$_3$ catalyst sold under the name T-4581 material by Süd-Chemie, with a typical composition of 61% CuO, 28% ZnO, and 10% Al$_2$O$_3$. The reactor was pressurized with nitrogen to 300 psig, and then vented to ambient. The reactor pressure was maintained by means of a backpressure controller. The nitrogen purge was repeated two additional cycles, followed by three hydrogen purges. The reactor was then fed hydrogen at 500 scc/m and 300 psig. The reactor was heated, at 1° C./minute with a resistance heater, to 250° C. and held at that temperature for 4 hr to reduce the catalyst. The temperature and pressure were set as shown in the following table. The hydrogen flow, metered via a mass flow controller, was adjusted to provide a 4/1 molar ratio of H$_2$/DMAEE. DMAEE was fed to the reactor under pressure, via a constant flow syringe pump. MMA was co-fed to the reactor under pressure, via a constant flow syringe pump, at an MMA/DMAEE molar ratio of 2/1. Effluent from the reactor was analyzed by GC. The results obtained at two variations of this example are displayed in Table 2, where performance characteristics are those defined in Example 1 above.

TABLE 2

| Ex. | DMAEE feed, ml/hr | T, °C. | P, psig | DMAEE Conversion, % | TMAEE Selectivity, % | TMAEE Yield, % | Productivity, g TMAEE/ g-cat-hr |
|---|---|---|---|---|---|---|---|
| 4A | 9.96 | 200 | 69.3 | 70.9 | 70.3 | 49.9 | 0.56 |
| 4B | 16.36 | 200 | 69.7 | 55.7 | 79.3 | 44.0 | 0.81 |

This alternate CuO/ZnO catalyst, relative to the Example 2 catalyst, showed slightly better TMAEE selectivity and slightly lower reactor productivity.

Example 5

Vapor Phase Amination of DMAEE with MMA to Produce TMAEE in a Continuous Fixed Bed Reactor with CuO/ZnO Catalysts of Varying Cu/Zn Ratio A fixed bed tubular reactor, equipped with a 10 cc quartz preheat bed, was charged with approximately 8 cc of a CuO/ZnO catalyst sold under the name T-4322 by Süd-Chemie (with nominally 50% Cu and 20% Zn), and a Cu-0891 catalyst from Engelhard (with nominally 27% Cu and 33% Zn). These catalysts are referred to as 5A, and 5B, respectively. The reactor was pressurized with nitrogen to 300 psig, and then vented to ambient. The reactor pressure was maintained by means of a backpressure controller. The nitrogen purge was repeated through two additional cycles, followed by three hydrogen purges. The reactor was then fed hydrogen at 500 scc/m and 300 psig. The reactor was heated, at 1° C./minute with a resistance heater, to 250° C. and held at that temperature for 4 hr to reduce the catalyst. The temperature and pressure were set as shown in Table 3. The hydrogen flow, metered via a mass flow controller, was adjusted to provide a 4/1 molar ratio of $H_2$/DMAEE. DMAEE was fed to the reactor under pressure, via a constant flow syringe pump. MMA was co-fed to the reactor under pressure, via a constant flow syringe pump, at an MMA/DMAEE molar ratio of 2/1. Effluent from the reactor was analyzed by GC. The results obtained at two variations of this example are displayed in the following table, where performance characteristics are those defined in Example 1 above.

C., followed by calcination for 2 hours at 400° C. The resultant catalyst powder was then pelletized and classified to +16/−20 mesh, and stored for use in the synthesis reaction. This catalyst, referred to as 6A, contained approximately 1% La by weight. Catalysts with different promoters were made as described for the La-doped material by substituting the requisite quantities of the appropriate nitrate salt precursor. Catalysts, prepared at the 1% promotion levels, are designated as 6B, 6C, 6D, 6E, 6F, and 6G, for Cs, K, Mg, Pt, Ir, and Re, respectively.

Synthesis Reactions: A fixed bed tubular reactor, equipped with a 10 cc quartz preheat bed, was charged with approximately 8 g of the promoted CuO/ZnO catalyst described above. The reactor was pressurized with nitrogen to 300 psig, and then vented to ambient. The reactor pressure was maintained by means of a backpressure controller. The nitrogen purge was repeated two additional cycles, followed by three hydrogen purges. The reactor was then fed hydrogen at 500 scc/m and 300 psig. The reactor was heated, at 1° C./minute with a resistance heater, to 250° C. and held at that temperature for 4 hr to reduce the catalyst. The temperature

TABLE 3

| Ex. | Cu/Zn wt/wt in catalyst | DMAEE feed, mL/hr | T, ° C. | P, psig | DMAEE Conversion, % | TMAEE Selectivity, % | TMAEE Yield, % | Productivity, g TMAEE/ g-cat-hr |
|---|---|---|---|---|---|---|---|---|
| 2A | 1.9 | 14.22 | 199 | 70.5 | 74.6 | 69.1 | 51.6 | 0.79 |
| 2B | 1.9 | 21.33 | 202 | 67 | 55.3 | 74.7 | 41.3 | 0.95 |
| 4A | 2.2 | 9.96 | 200 | 69.3 | 70.9 | 70.3 | 49.9 | 0.56 |
| 4B | 2.2 | 16.36 | 200 | 69.7 | 55.7 | 79.3 | 44.0 | 0.81 |
| 5A | 2.5 | 14.22 | 200 | 70 | 66.5 | 77.8 | 51.8 | 0.89 |
| 5B | 0.82 | 5.33 | 200 | 70.3 | 73.5 | 86.2 | 63.4 | 0.39 |

These experimental data show that these alternate CuO/ZnO catalysts of varying Cu/Zn ratio can be used advantageously in fixed bed, continuous vapor phase operation, relative to the batch, liquid phase operation of Example 1.

Example 6

Vapor Phase Amination of DMAEE with MMA to Produce TMAEE in a Continuous Fixed Bed Reactor with Promoted CuO/ZnO Catalysts Preparation of promoted versions of the CuO/ZnO catalyst: A 0.62-g portion of $La(NO_3)_2 \cdot 6H_2O$ was dissolved in 5 ml of deionized (DI) water. A 20-g portion of the CuO/ZnO catalyst used in Example 4 was crushed to a −35 mesh powder, and added to the salt solution. The mixture was stirred well, and the material was dried for 2 hours at 110° and pressure were set as shown in the following table. The hydrogen flow, metered via a mass flow controller, was adjusted to provide a 4/1 molar ratio of $H_2$/DMAEE. DMAEE was fed to the reactor under pressure, via a constant flow syringe pump. MMA was co-fed to the reactor under pressure via a constant flow syringe pump, at an MMA/DMAEE molar ratio of 2/1. Effluent from the reactor was analyzed by GC. The results obtained for seven variations of this example, corresponding to the seven promoted catalysts described above, are displayed in Table 4, where performance characteristics are those defined in Example 1 above. Also displayed, for reference, are the results from the unpromoted catalyst described in Example 4. The table also provides two additional measures of catalyst selectivity, namely the weight ratios of desired product TMAEE to key byproducts BDMAEE and NMM.

TABLE 4

| Ex. Promoter | T, ° C. | P, psig | DMAEE Conversion, % | TMAEE Selectivity, % | TMAEE/ BDMAEE, wt/wt | TMAEE/ NMM, wt/wt |
|---|---|---|---|---|---|---|
| 4A None | 200 | 69.3 | 70.9 | 70.3 | 13.0 | 31.4 |
| 4B None | 200 | 69.7 | 55.7 | 79.3 | 26.0 | 84.4 |
| 6A La | 200 | 72.2 | 64.2 | 88.7 | 53.5 | 264.3 |
| 6B Cs | 200 | 70.8 | 58.4 | 90.5 | 142.3 | 166.1 |
| 6C K | 200 | 70.3 | 55.1 | 91.2 | 173.4 | 250.0 |
| 6D Mg | 200 | 74.2 | 60.0 | 87.9 | 44.0 | 139.6 |
| 6E Pt | 201 | 71.5 | 46.6 | 61.3 | 6.0 | 26.2 |

TABLE 4-continued

| Ex. | Promoter | T, °C. | P, psig | DMAEE Conversion, % | TMAEE Selectivity, % | TMAEE/ BDMAEE, wt/wt | TMAEE/ NMM, wt/wt |
|---|---|---|---|---|---|---|---|
| 6F | Ir | 202 | 70.8 | 64.3 | 39.8 | 1.6 | 4.3 |
| 6G | Re | 202 | 69.5 | 59.4 | 69.6 | 11.5 | 22.2 |

These data show that addition of La, Cs, K, or Mg promoters to the base CuO/ZnO catalyst had a significant positive impact on selectivity. At similar conversions, these promoted catalyst showed higher overall selectivity, and significantly higher TMAEE/BDMAEE and TMAEE/NMM ratios. The Pt, Ir, and Re promoted catalysts had the opposite effect of reducing selectivity. These results indicate that adding promoters, chosen from the Group 1 or 2 elements, or early lanthanides, to the base CuO/ZnO catalysts, can result in a substantial improvement in catalyst selectivity for the amination of amino ether alcohols.

Example 7

Vapor Phase Amination of DMAEE with MMA to Produce TMAEE in a Continuous Fixed Bed Reactor with Cu/Cr Catalyst A fixed bed tubular reactor, equipped with a 10 cc quartz preheat bed, was charged with approximately 8 g of a Cu/Cr catalyst (G-13 A, from Süd-Chemie, with a typical composition of 40% Cu and 26% Cr). The reactor was pressurized with nitrogen to 300 psig, and then vented to ambient. The reactor pressure was maintained by means of a backpressure controller. The nitrogen purge was repeated two additional cycles, followed by three hydrogen purges. The reactor was then fed hydrogen at 500 scc/m and 300 psig. The reactor was heated, at 1° C./minute with a resistance heater, to 250° C. and held at that temperature for 4 hr to reduce the catalyst. The temperature and pressure were set as shown in the following table. The hydrogen flow, metered via a mass flow controller, was adjusted to provide a 4/1 molar ratio of H$_2$/DMAEE. DMAEE was fed to the reactor under pressure, via a constant flow syringe pump. MMA was co-fed to the reactor under pressure via a constant flow syringe pump, at an MMA/DMAEE molar ratio of 2/1. Effluent from the reactor was analyzed by GC. The results obtained for this example are displayed in Table 5, where performance characteristics are those defined in Example 1 above. Also displayed, for reference, are the results from the unpromoted catalyst described in Example 4. The table also provides two additional measures of catalyst selectivity in the weight ratio of desired product TMAEE to key byproducts BDMAEE and NMM.

The Cu/Cr catalyst had poorer selectivity performance, relative to the CuO/ZnO catalyst. At similar conversions, this catalyst showed lower overall selectivity, and significantly lower TMAEE/BDMAEE and TMAEE/NMM ratios. These results indicate that CuO/ZnO catalyst usage unexpectedly results in a substantial improvement in catalyst selectivity for the amination of amino ether alcohols, relative to known copper catalysts, when used in a vapor phase process.

Although the invention is illustrated and described herein with reference to specific embodiments, the invention is not intended to be limited to the details shown. Rather, it is intended that the claims which follow be construed to include all embodiments and modifications of the invention which may be made by those skilled in the art to which this invention pertains, without departing from the true spirit and scope of the invention.

The invention claimed is:

1. A method for converting an amino ether alcohol to an amino ether amine, the method comprising contacting a catalyst comprising at least one of zinc oxide or a zinc salt, and at least one of copper oxide or a copper salt, with a vapor phase mixture comprising the amino ether alcohol and an amine, wherein the amino ether alcohol has the formula NR$^1$R$^2$R$^3$, wherein R$^1$ and R$^2$ each individually is selected from the group consisting of H, C1–C10 alkyl, a C6–C10 aryl, and a C6–C10 aralkyl R$^3$ is a C4–C10 alkyl group having within it an ether linkage and also containing at least one hydroxyl group, and the amine has the formula, NHR$^4$R$^5$, wherein R$^4$ and R$^5$ each individually is H, a C1–C10 alkyl, a C6–C10 aryl, or a C6–C10 aralkyl group, provided that no more than one of R$^4$ and R$^5$ is H, wherein the contacting is performed at a temperature ranging from 120° C. to 300° C. and a pressure ranging from 0 to 500 psig (101 to 3549 kPa).

2. The method of claim 1, wherein the contacting is performed at a temperature ranging from 180° C. to 220° C. and a pressure ranging from 0 to 100 psig (101 to 791 kPa).

3. The method of claim 2, wherein the contacting is performed at a pressure of 40 to 80 psig (377 to 653 kPa).

4. The method of claim 1, wherein the contacting is performed in a fixed bed tubular reactor.

5. The method of claim 1, wherein a weight ratio of copper to zinc in the catalyst ranges from 0.3 to 6.

6. The method of claim 1, wherein a weight ratio of copper to zinc in the catalyst ranges from 0.4 to 3.

TABLE 5

| Ex. | Catalyst Type | T, °C. | P, psig | DMAEE Conversion, % | TMAEE Selectivity, % | TMAEE/ BDMAEE, wt/wt | TMAEE/ NMM, wt/wt |
|---|---|---|---|---|---|---|---|
| 4A | CuO/ZnO | 200 | 69.3 | 70.9 | 70.3 | 13.0 | 31.4 |
| 4B | CuO/ZnO | 200 | 69.7 | 55.7 | 79.3 | 26.0 | 84.4 |
| 7 | Cu/Cr | 200 | 69.8 | 67.2 | 58.1 | 4.2 | 4.9 |

7. The method of claim 1, wherein the catalyst further comprises a promoter comprising at least one of an alkali metal, an alkaline earth metal, lanthanum, cerium, praseodymium, neodymium, samarium, europium, gadolinium or terbium, the promoter present at 0.05 to 5 wt %, based on a total weight of the catalyst.

8. The method of claim 8, wherein the promoter is present at 0.2 to 2 wt %, based on the total weight of the catalyst.

9. The method of claim 7, wherein the promoter is present at 0.3 to 1.5 wt %, based on the total weight of the catalyst.

10. The method of claim 7, wherein the promoter comprises at least one of potassium, rubidium or cesium.

11. The method of claim 7, wherein the promoter comprises at least one of magnesium, calcium or strontium.

12. The method of claim 7, wherein the promoter comprises at least one of lanthanum, cerium, or praseodymium.

13. The method of claim 7, wherein the catalyst further comprises at least one of $Al_2O_3$ or $SiO_2$.

14. The method of claim 7 wherein the method further comprises, prior to said contacting, treating the catalyst with hydrogen under conditions sufficient to form an activated catalyst.

15. The method of claim 14 wherein the hydrogen is generated by interaction of the catalyst with an organic compound.

16. The method of claim 7 wherein the vapor phase mixture further comprises hydrogen.

17. A method for converting dimethylaminoethoxyethanol to an amino ether amine, the method comprising:

contacting a catalyst with hydrogen gas to produce an activated catalyst; and contacting the activated catalyst with a vapor phase mixture comprising dimethylaminoethoxyethanol and at least one of methylamine or dimethylamine;

wherein the catalyst comprises the following materials in the following amounts, based on the total catalyst weight:

20 to 70 wt% copper oxide, 20 to 65 wt% zinc oxide, and 0.3 to 1.5 wt% of at least one of potassium or cesium.

* * * * *